United States Patent [19]

Ramachandran et al.

[11] Patent Number: 5,015,756
[45] Date of Patent: * May 14, 1991

[54] PROCESS FOR THE PRODUCTION OF NITRILES

[75] Inventors: Ramakrishnan Ramachandran, Allendale; Yagya Shukla, Roselle Park; Donald L. MacLean, Annandale, all of N.J.

[73] Assignee: The BOC Group, Inc., New Providence, N.J.

[*] Notice: The portion of the term of this patent subsequent to Sep. 19, 2006 has been disclaimed.

[21] Appl. No.: 345,916

[22] Filed: May 1, 1989

Related U.S. Application Data

[63] Continuation-in-part of Ser. No. 216,037, Jul. 7, 1988, Pat. No. 4,868,330, which is a continuation-in-part of Ser. No. 178,117, Apr. 6, 1988, abandoned, which is a continuation-in-part of Ser. No. 124,731, Nov. 24, 1987, abandoned.

[51] Int. Cl.$^5$ .................. C07C 253/24; C07C 253/26
[52] U.S. Cl. ..................................... 558/320; 558/319; 558/323; 558/324; 558/325; 558/326; 558/327
[58] Field of Search ............... 558/319, 320, 327, 323, 558/324, 325, 326

[56] References Cited

U.S. PATENT DOCUMENTS

| | | | |
|---|---|---|---|
| 3,176,444 | 4/1965 | Kiyonaga | 55/26 |
| 3,591,620 | 7/1971 | Yoshino et al. | 260/465.3 |
| 3,914,277 | 10/1975 | Wood | 260/465.3 |
| 4,070,393 | 1/1978 | Angstadt et al. | 260/465.3 |
| 4,335,056 | 6/1982 | Callahan et al. | 562/545 X |
| 4,498,910 | 2/1985 | Benkmann | 585/321 X |
| 4,609,502 | 9/1986 | Khoobiar et al. | 558/320 |
| 4,863,330 | 9/1989 | Ramachandran et al. | 558/320 |

FOREIGN PATENT DOCUMENTS 0318205  5/1989  European Pat. Off. .
1336135 11/1973  United Kingdom .

OTHER PUBLICATIONS

Gates, et al., "Chemistry of Catalytic Processes", McGraw-Hill, (1979), pp. 349-350 and pp. 380-384.
Thomas, "Catalytic Processes and Proven Catalysts," Academic Press, (1970), pp. 118-119.

*Primary Examiner*—Joseph Paul Brust
*Attorney, Agent, or Firm*—Carol A. Nemetz; Robert I. Pearlman

[57] ABSTRACT

An improved process is provided for the production of nitriles from hydrocarbons by reaction with an oxygen-containing gas comprising oxygen, air or a gas enriched in oxygen relative to air and ammonia in the presence of a suitable catalyst. In the process, a selective separator provides recycle of a substantial portion of the unreacted hydrocarbon as well as for a controlled amount of a gaseous flame suppressor in the system. The gaseous flame suppressor comprises a substantially unreactive hydrocarbon containing 1 to 5 carbon atoms, carbon dioxide and nitrogen when present in the feed to the ammoxidation reactor. The use of air or oxygen-enriched air in the feed to the ammoxidation reactor is particularly advantageous from an economic view in combination with a pressure swing adsorption unit as the selective separator. The process is characterized by high selectivity to the formation of the product.

21 Claims, 5 Drawing Sheets

FIG. 5

PROCESS FOR THE PRODUCTION OF NITRILES

RELATED APPLICATION

This application is a continuation-in-part of U.S. patent application Ser. No. 07/216,037 filed July 7, 1988, now U.S. Pat. No. 4,868,330, which, in turn is a continuation-in-part of U.S. patent application Ser. No. 07/178,117, filed Apr. 6, 1988, now abandoned, which, in turn, is a continuation-in-part of U.S. patent application Ser. No. 07/178,117, filed Apr. 6, 1988, now abandoned, which, in turn, is a continuation-in-part of U.S. patent application Ser. No. 07/124,731, filed Nov. 24, 1987 and now abandoned.

FIELD OF THE INVENTION

The present invention is directed to a process for producing nitriles from hydrocarbons, an oxygen-containing gas and ammonia in the presence of a suitable catalyst under conditions which achieve high efficiency and selectively toward the desired product.

BACKGROUND OF THE INVENTION

The production of nitriles by ammoxidation of an appropriate hydrocarbon in the presence of a suitable catalyst is well known. The production of acrylonitrile, for example, from a gaseous feed of propylene, ammonia and air is described by Bruce C. Gates et al. in *Chemistry of Catalytic Processes*, McGraw-Hill (1979), at 380-384.

The feed is sent to an ammoxidation reactor where, in the presence of a suitable catalyst, acrylonitrile is produced along with lesser amounts of other nitrogen-containing compounds. The effluent from the ammoxidation reaction is quenched with water and the desired products are obtained in the liquid phase. The gas phase by-products, typically oxygen, carbon dioxide, carbon monoxide and unreacted hydrocarbon, are combined with natural gas and sent to a boiler for combustion as disclosed, for example, in Yoshino et al., U.S. Pat. No. 3,591,620 and Callahan et al., U.S. Pat. No. 4,335,056.

More recently, Khoobiar et al., in U.S. Pat. No. 4,609,502 disclosed a cyclic process for producing acrylonitrile using propane as a starting material which is initially dehydrogenated catalytically in the presence of steam to form propylene. This is in contrast to most conventional dehydrogenation processes which avoid steam primarily due to the costs involved. After ammoxidation, the effluent is quenched, the desired product removed, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are by-products of dehydrogenation, and unreacted propylene in addition to carbon oxides. As an option, this gas mixture is split and a portion is sent to a separator which removes only carbon dioxide. A portion of the effluent from the separation is purged to remove light hydrocarbons. The nonpurged stream is mixed with the remainder of the oxidator effluent, fresh propane and steam, if necessary, and sent to the dehydrogenator where the propane is converted to propylene. Another option is to cool and liquify the $C_3$ hydrocarbons therefrom and then vaporize them prior to recycle.

The aforementioned process suffers from several disadvantages. The amount of propane which is converted to propylene is only in the range of about 20 percent to 60 percent per pass, typically about 40 percent, and therefore, about 60 percent of the propane feed is recycled throughout the system. At conventional velocities, the presence of such large amounts of propane along with hydrogen and other gases can produce higher pressures in the ammoxidation reaction zone which can, in turn, result in decreased yields of acrylonitrile. This problem could be overcome by using a more efficient dehydrogenation catalyst, if such were commercially available. Also, there is no practical way in this scheme to selectively remove by-products of propane dehydrogenation, such as methane, ethane, ethylene and the like, thereby preventing their accumulation in the system. Providing a purge stream to remove these gases will also cause removal of some of the circulating propane and propylene. As the process is being carried on in a continuous manner, this loss of starting material causes a significant decrease in the yield of propylene. It is disclosed that propane and propylene are recovered from the purge stream prior to venting. Additional refrigeration is therefore necessary to liquify the propane and propylene. This apparatus, as well as that required to vaporize them prior to recycle, significantly adds to the capital cost of the process.

Another disadvantage of the Khoobiar et al. process stems from the use of the selective oxidation reactor to treat the gaseous effluent from the quencher. The gases exiting the quencher are at ambient temperature and must be heated prior to introduction into the oxidation reactor in order to promote oxygen removal. Because there is a significant amount of oxygen in the quencher effluent, the heat of reaction generated in the oxidation reactor can result in excessive temperatures in the system. There are three options to alleviate this problem. First, the amount of oxygen entering the oxidation reactor can be reduced by other means. Second, multiple reactors can be utilized with a cooling means between each pair of reactors. Third, a portion of the effluent from the reactor is passed through a cooling means and recycled to the feed to reduce the internal temperature of the reactor. None of these measures is attractive from the viewpoint of cost and efficiency.

The oxidation reactor in the Khoobiar et al. process is operated with oxidation catalysts such as noble metals (e.g., platinum). Olefins and carbon monoxide, which are generated in the dehydrogenation reactor, are known to poison these catalysts, as disclosed in *Catalytic Processes and Proven Catalysts*, Charles L. Thomas, Academic Press (1970), at 118-119. Accordingly, multiple oxidation reactors must be used to allow for frequent regeneration of the catalyst which represents yet another addition to production costs (U.S. Pat. No. 4,609,502, at column 4, lines 51-56).

It is therefore apparent that industry is still searching for a cost effective process of converting hydrocarbons into nitriles. Applicants have discovered a process which is cost effective and in which the disadvantages of the aforementioned systems are substantially reduced or eliminated. Moreover, in comparison to conventional processes, the thermal requirements of Applicants' process are markedly reduced.

SUMMARY OF THE INVENTION

A process is disclosed for the production of nitriles comprising reacting in a suitable reactor a hydrocarbon, an oxygen-containing gas, preferably oxygen-enriched air, and ammonia gas in the presence of a suitable catalyst under operating conditions which produce the desired product at relatively low conversion per pass and relatively high selectivity. The product stream is quenched with a liquid to form a liquid phase containing the desired product and a gas phase which is introduced into a suitable selective separator, preferably a pressure swing adsorption unit, to separate substantially all of the unreacted hydrocarbon which is recycled to the reactor. The process provides an effective amount of a gaseous flame suppressor, i.e. from about 30 to about 95 percent by volume, in the gas stream which is introduced into the selective separator.

DESCRIPTION OF THE PREFERRED EMBODIMENTS

In the process of this invention a hydrocarbon is reacted with an oxygen-containing gas comprising pure oxygen, air or a gas enriched in oxygen relative to air in the presence of an ammoxidation catalyst to form a nitrile. Suitable ammoxidation catalysts are those that will catalyze the production of the desired nitrile under the conditions utilized in the reactor. These catalysts and their use are conventional and well known to one of ordinary skill in the art. The term "hydrocarbon" as utilized herein includes both aliphatic and aromatic compounds. Preferably, hydrocarbon starting materials are olefins or xylenes although formation of a nitrile directly from an alkane by appropriate choice of catalyst is clearly within the scope of the present invention. Alpha, beta olefinically unsaturated nitriles are produced from alkanes and alkenes and benzene dinitriles are produced from xylenes with the former being preferred.

Illustrative of products, and their respective starting materials, which can be advantageously produced by the method of this invention are acrylonitrile from propylene or propane, methacrylonitrile from isobutylene or isobutane, phthalonitrile from o-xylene (that is, orthoxylene), and the like. In the interest of brevity, the subject process will be described with reference to the production of acrylonitrile from propylene, but is in no way intended to be limited thereto.

Figure 1:
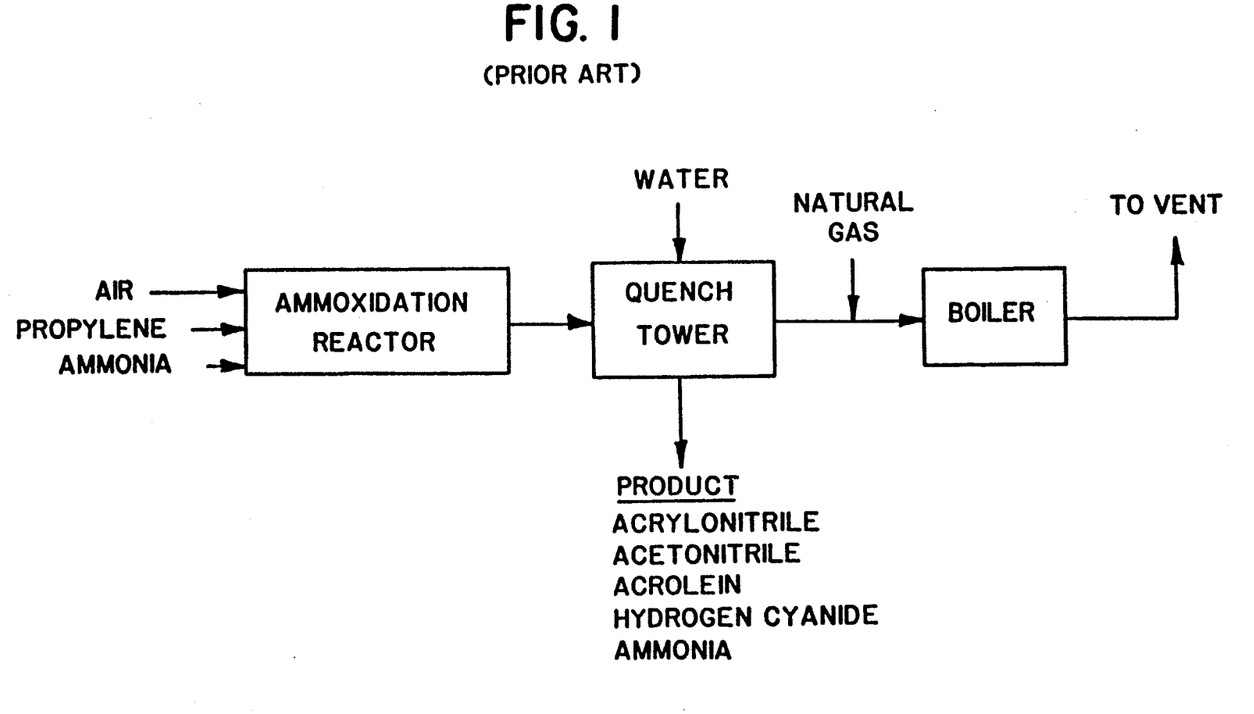
FIG. 1 illustrates in a block diagram a present conventional process of producing acrylonitrile.

Turning to the drawings, a process currently utilized commercially to produce acrylonitrile is illustrated in FIG. 1. Propylene, ammonia and air are fed into a conventional reactor containing a suitable ammoxidation catalyst. The reactor may be of any conventional fixed or fluidized bed design, typically the latter. Such processes, which do not involve a recycle step, can utilize air or oxygen-enriched air in the reactor feed, although air is normally used for reasons of economy. The oxygen concentration in the reactor feed is not considered critical with regard to the accumulation of other gases, primarily nitrogen, in the system due to the lack of recycle. Those skilled in the art are aware that the oxygen content in the feed in such a process must be regulated in regard to other aspects of the process.

The reactor product gases are cooled in a heat exchanger, not shown, to form steam and then passed to a water quench column or tower to dissolve the products, i.e. acrylonitrile, acetonitrile, acrolein and hydrogen cyanide as well as unreacted ammonia. The acrylonitrile is subsequently recovered from the aqueous solution by conventional methods. The off-gases from the quench tower are combined with natural gas and combusted in a boiler to generate steam. The off-gases of the boiler are vented. Since there is no recycle provided in such a process, the yield of acrylonitrile realized is directly related to the efficiency of the reactor.

Figure 2:
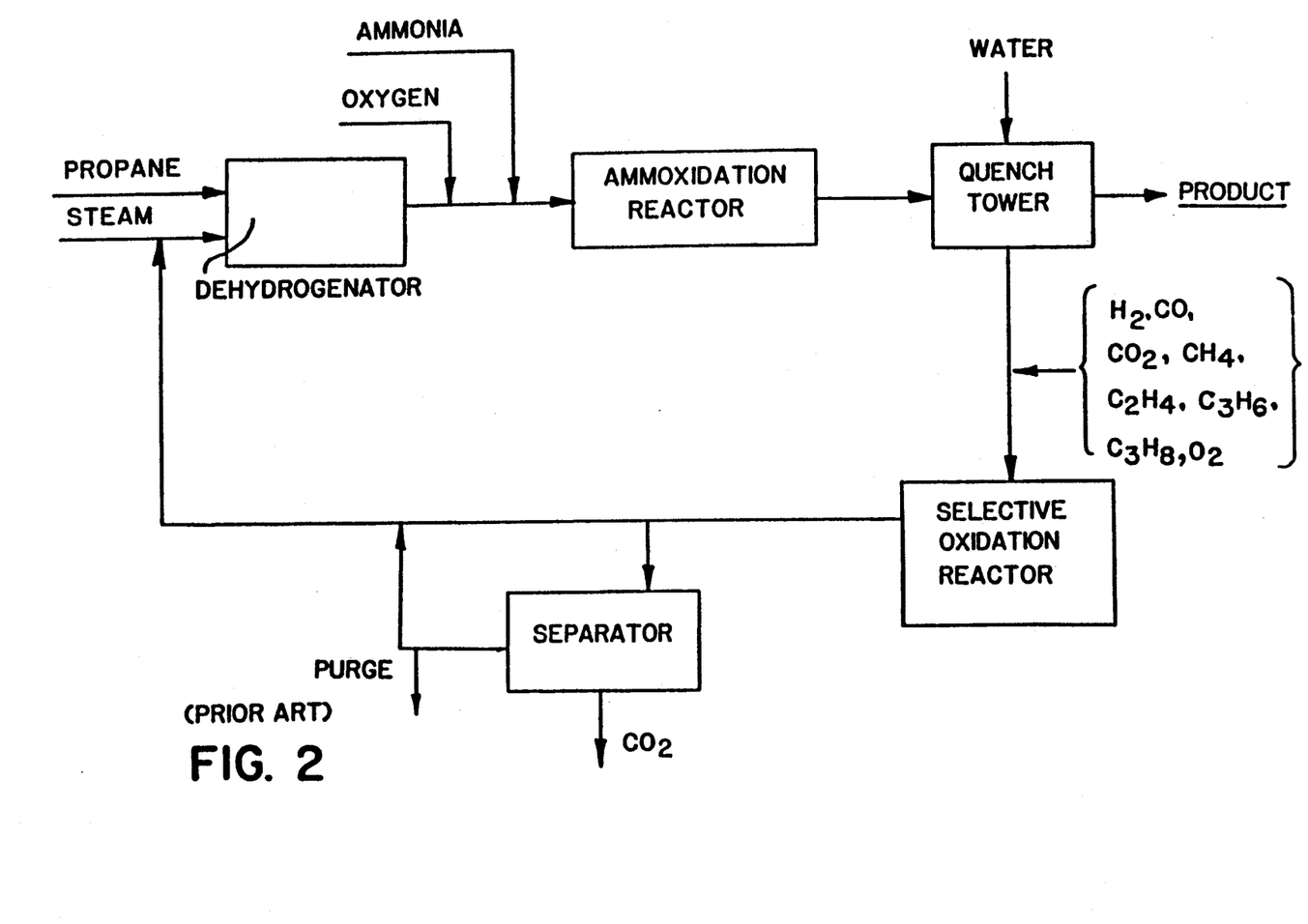
FIG. 2 illustrates in a block diagram a prior art process of producing acrylonitrile utilizing a recycle step.

FIG. 2 illustrates the cyclic process for producing acrylonitrile from propane disclosed in Khoobiar et al., U.S. Pat. No. 4,609,502. In this process, propane and steam are fed into a dehydrogenator to form propylene which is then mixed with oxygen and ammonia and fed into an ammoxidation reactor such as described in FIG. 1. The product is fed to an aqueous quench tower as in FIG. 1 and the products withdrawn in solution. The gaseous take-off from the quench tower, typically containing oxygen, hydrogen, carbon monoxide, carbon dioxide, methane, ethane, ethylene, propane and propylene, is fed to a selective oxidation reactor. As previously indicated, it is generally essential for the efficient operation of such a reactor to heat the gas mixture prior to introduction therein.

A portion of the off-gas from the oxidation reactor is passed to a separator to remove carbon oxides by an undisclosed mechanism. A portion of the separator effluent, which contains light hydrocarbons and hydrogen, is purged, treated to remove propane and propylene and discarded, thereby preventing build-up of by-products in the system. The propane and propylene are combined with the remainder of the separator and oxidator effluents and recycled to the dehydrogenator. It is, of course, necessary for the oxidator to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

In contrast to the processes illustrated in FIGS. 1 and 2, the process of the present invention provides a selective separator, preferably a pressure swing adsorption unit, which effectively removes a substantial portion of the reactant hydrocarbon so that it can be recycled to the ammoxidation reactor, thus providing high propylene conversion and economy of operation. As utilized herein, the expression "a substantial portion" as it pertains to recycle of the reactant hydrocarbon, means at least about 80 percent by volume where the oxygen-containing gas in the feed to the ammoxidation reactor is air, at least about 90 percent by volume where a mixture of equal parts of pure oxygen and air is utilized as the oxygen-containing gas and at least about 95 percent by volume where the oxygen-containing gas is pure oxygen. Of course, lesser amounts may be recycled but would reduce the efficiency of the process thereby increasing, e.g., waste gas cleanup and raw material costs. In each instance, these are minimum percents. Utilizing pure oxygen as the oxygen-containing gas, for example, the amount of reactant hydrocarbon recycled is typically 97-99 percent by volume.

As the selective separator contemplated herein typically requires a pressurized feed, the process of the present invention provides an effective amount of a gaseous flame suppressor to mimimize the flammability potential at the point or points in the cycle where the pressure is increased. Although it is preferred to locate the compressor in gaseous effluent from the quench tower, it may be at other appropriate locations in the cycle, for example, a compressor may be located in the outlet of the separator. There may be only one compressor, or more may be present. The gaseous flame suppressor of the present invention comprises a substantially unreactive hydrocarbon having from 1 to 5 carbon atoms, carbon dioxide and, where air or enriched air is utilized as the oxygen-containing gas in the feed to the ammoxidation reactor, nitrogen. By "substantially unreactive" is meant that at least 90 percent by volume of the hydrocarbon component of the gaseous flame suppressor will pass through the ammoxidation reactor unchanged. The substantially unreactive hydrocarbon can be a saturated or unsaturated hydrocarbon with saturated being preferred.

The amount of the gaseous flame suppressor mixture in the subject cyclic process is controlled so that it will be maximized at the point or points in the system where it is of greatest advantage, i.e. the feed to the pressure raising means. By "maximize" is meant that the amount of flame suppressor is optimum to achieve a minimum flammability potential with a margin of safety within the constraints of the systems, i.e. without sacrifice of the primary object of efficiently producing the desired nitrile.

The amount of the gaseous flame suppressor is such that, regardless of the location of the means to increase pressure, the gaseous effluent from the quench tower will contain from about 30 to about 95 percent by volume thereof. It will be appreciated that, when pure oxygen is utilized as the oxygen-containing gas in the feed to the ammoxidation reactor, nitrogen will not be a component in the gaseous flame suppressor. In embodiments of the subject process to be described herein, each of the components of the gaseous flame suppressor mixture of the present invention will comprise a major portion thereof.

Examples of specific substantially unreactive hydrocarbons utilized as a component of the subject gaseous flame suppressor and the reaction in which they are utilized include: propane for the production of acrylonitrile from propylene, methane or isobutane for the production of acrylonitrile from propane; n-butane for the production of methacrylonitrile from iso-butylene; methane for the production of methacrylonitrile from isobutane; and the like.

Unreacted hydrocarbon reactant, e.g. propylene, isobutylene and the like, while not a major portion of the gaseous flame suppressor, appears to enhance the flame suppressant capacity thereof. The amount of unreacted reactant hydrocarbon present in the gaseous flame suppressor mixture will depend on the percent per-pass conversion of the reactant hydrocarbon entering the ammoxidation reactor which is converted to products. Those skilled in the art will appreciate that factors such as choice of catalyst, operating temperatures and the like can be adjusted to have the ammoxidation reactor operate at a desired conversion of the reactant hydrocarbon in the feed thereto. At lower operating conversions, e.g. 60 percent conversion, there will be a greater amount of unreacted reactant hydrocarbon circulating in the system. For example, using substantially pure oxygen in an ammoxidation reactor operating at 80 percent conversion in accordance with the invention, there will be only about 10 to 15 percent unreacted reactant hydrocarbon in the quench tower effluent whereas, at 60 and 90 percent conversion, there will be a greater and lesser percent, respectively, of unreacted reactant hydrocarbon in the quench tower effluent. The composition of the gaseous flame suppressor will be adjusted accordingly.

The process of this invention is advantageous in that it provides the efficiency of recycle afforded by the process illustrated in FIG. 2, yet is free of the disadvantages inherent therein while, at the same time, being less complex. The advantages of the present invention are, in large measure, provided by the incorporation into the process of a selective separator which retains a substantial portion of the unreacted reactant hydrocarbon in the system. The gaseous flame suppressor of the subject process may be partially or totally recycled, depending on the operating conditions and feed to the system. In a preferred embodiment, the separator is a pressure swing adsorption unit.

The efficiency of the selective separator of the present invention permits operation of the system at a low conversion, i.e. a reduction from the conventional object of achieving the highest possible once thru yield of feed material to products. Reducing conversion will, in turn, increase selectivity with a given catalyst. A substantial economic benefit is realized on an industrial scale even from a one percent increase in selectivity to the desired product, which is achieved by the present process since it retains and recycles a very high percentage of unreacted reactant hydrocarbon. Reducing conversion from the present levels of about 97% to about 90% will result in about one percent increase in selectivity. Therefore, in the context of the present invention, a level of conversion below the maximum such that at least about one percent increase in selectivity with a given catalyst is achieved is low conversion. Low conversion as utilized herein, therefore, can be 90 percent or even higher if the desired increase in selectivity is produced.

Conversion per pass, selectivity and yield utilized in the above discussion are defined as follows:

$$\text{Conversion Per Pass} = \frac{H_R}{H_F} \times 100$$

$$\text{Selectivity} = \frac{P_P}{H_R} \times 100$$

$$\text{Yield} = \frac{P_P}{H_F} \times 100$$

where
$H_R$ = moles of reactive hydrocarbon reacted
$H_F$ = moles of reactive hydrocarbon fed
$P_P$ = moles of desired product produced Pressure swing adsorption (PSA) is a well known process for separating the components of a mixture of gases by virtue of the difference in the degree of adsorption among them on a particulate adsorbent retained in a stationary bed. Typically, two or more such beds are operated in a cyclic process comprising adsorption under relatively high pressure and desorption or bed regeneration under relatively low pressure or vacuum. The desired component or components may be obtained during either of these stages. The cycle may contain other steps in addition to the fundamental steps of adsorption and regeneration, and it is commonplace to have two or more adsorbent beds cycled 180° out of phase to assure a pseudo continuous flow of desired product. While it is conventional for the adsorption step of a PSA cycle to be carried out under pressure, it can run at ambient pressure with desorption under vacuum. It is the difference in pressure between the adsorption and desorption stages which is essential for operation of the system.

Figure 3:
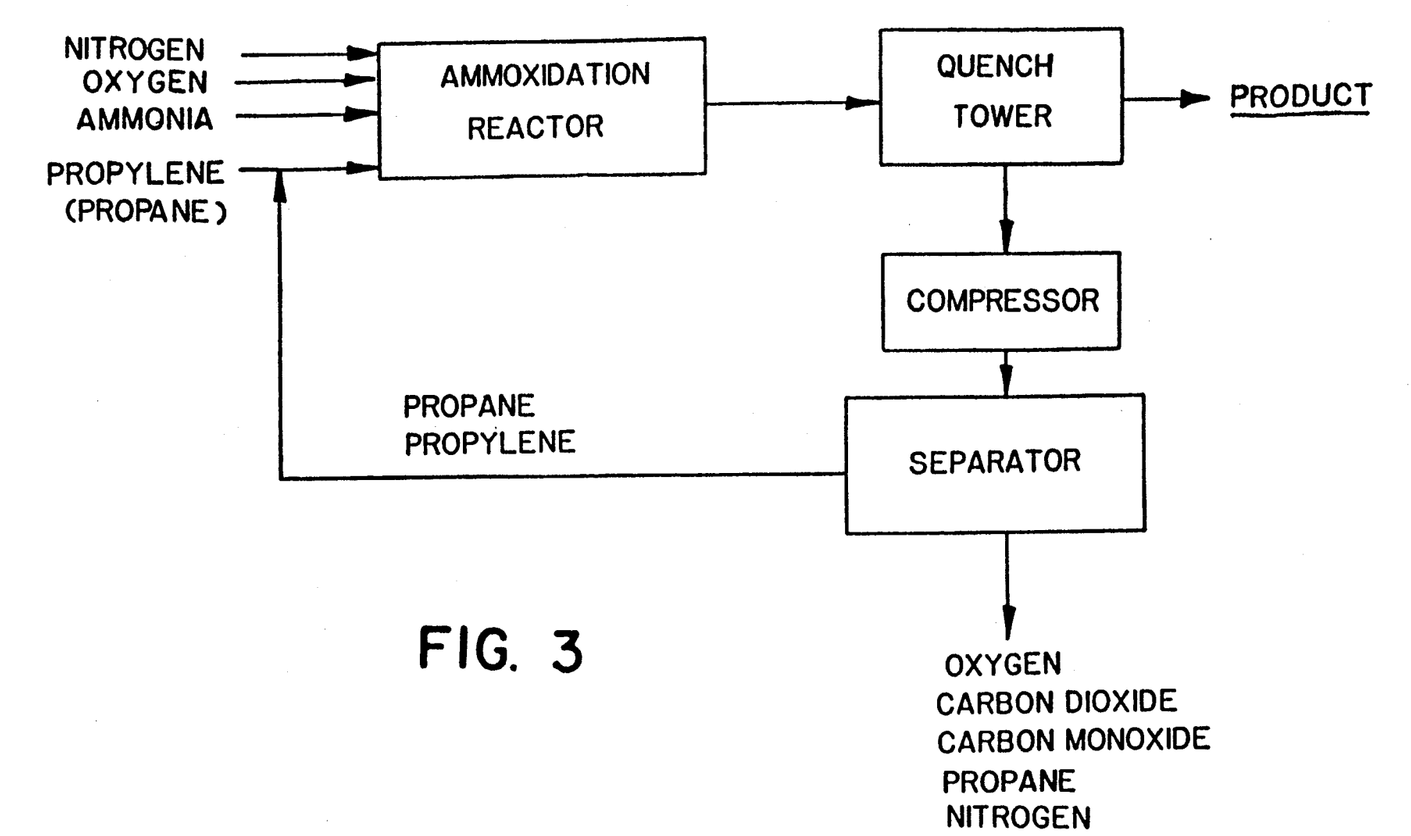
FIG. 3 illustrates in a block diagram an embodiment of a process for producing acrylonitrile in accordance with the present invention utilizing air or oxygen-enriched air as a feed to the ammoxidation reactor, a pressure swing adsorption unit as the separator wherein the gaseous flame suppressor contains a major portion of nitrogen.

Referring to FIG. 3 and a process for producing acrylonitrile, a feed into a conventional ammoxidation reactor comprises propylene, ammonia and air or oxygen-enriched air. In accordance with this invention, oxygen-enriched air preferably contains from about 30 to 80, most preferably from about 55 to 65, percent by volume of oxygen. Such mixtures may be produced by adjusting the capacity of a conventional oxygen-producing unit, e.g. a conventional PSA unit, or by mixing pure oxygen with air in the proper proportions. The use of oxygen-enriched air will produce a minimum concentration of nitrogen in the feed to the ammoxidation reactor of from about 10 to 20 percent by volume of the feed into the reactor depending on the operating conversion of the reactor as discussed above. The minimum concentration of nitrogen in the reactor feed will result in the desired level of nitrogen in the feed to the compressor for the PSA unit separator as discussed hereafter.

The ammoxidation reactor utilized in the present process is conventional and may employ either a fixed or fluidized catalyst bed. A typical example of an ammoxidation reactor is disclosed in Angstadt et al., U.S. Pat. No. 4,070,393 and Gates et al., supra. at 381-383, each incorporated herein by reference. The reactor contains a conventional ammoxidation catalyst, such as bismuth-molybdenum oxide, iron-antimony oxide or uranium-antimony oxide, precipitated on silica and the like. Other suitable catalysts are disclosed, for example, in *Chemistry of Catalytic Processes*, Gates et al., McGraw Hill (1979), at 349-350 and Yoshino et al., U.S. Pat. No. 3,591,620, incorporated herein by reference. Additional suitable catalysts are known to those skilled in the art. For example, a vanadium-antimony oxide ammoxidation catalyst may be utilized when propane, rather than propylene, is the predominant feed stock (see Guttmann et al., U.S. Pat. No. 4,746,641).

The ammoxidation reaction is conducted at a temperature of from about 375° to 550° C., preferably from about 400° to 500° C., at low pressures, typically in the range of from about 2 to 30 psig, preferably from about 3 to 20 psig. The reactants are passed through the reactor at a relatively low velocity, typically in the range of from about 1.75 to 2.2 ft./sec. The ratio of oxygen to propylene in the feed is suitably in the range of 1.3:1 to 2.4:1 by volume. The ratio of ammonia to propylene in the feed is suitably in the range of 0.7:1 to 2.0:1 by volume.

The ammoxidation reaction results in the production of a major amount of acrylonitrile and minor amounts of acrolein, hydrogen cyanide, acetonitrile, and carbon oxides as well as unreacted oxygen, propylene and nitrogen. Commercially available propylene typically contains a small amount of propane unless additional costly processing is undertaken to remove it. This is advantageous since propane exerts a positive effect on the gaseous flame suppressor of the present process. In this embodiment, the propane is substantially recycled from the PSA unit. This gaseous mixture is quenched or scrubbed with a liquid, such as water, to dissolve the water soluble compounds for subsequent separation and recovery of acrylonitrile, acetonitrile and hydrogen cyanide. The off gases from the quench tower may be passed through another tower containing $H_2SO_4$ to remove $NH_3$ completely. In the following discussion, the quench tower off gas means the final off gas after the absorber, if it is also employed.

The gas phase effluent from the quench tower is introduced into a PSA unit separator wherein unreacted propylene is separated from the other gases in the mixture. Although the adsorption stage of the PSA unit can be at ambient pressure, it is preferred to pass the quench tower gaseous effluent through a compressor or other suitable means to increase the pressure thereof prior to introduction into the PSA unit. Experience has shown that the flammability potential in the system is greatest in the compressor. Therefore, the total amount of gaseous flame suppressor is at its maximum in the quench tower gaseous phase, i.e. the feed into the compressor, to minimize the flammability potential. The operating conditions of the system are adjusted to provide for this.

The gas phase effluent from the quench tower preferably contains, on a volume basis from about 1 to 3 percent of carbon monoxide, from about 3 to 5 percent of propylene, from about 6 to 8 percent of oxygen, from about 10 to 15 percent of carbon dioxide, from about 50 to 70 percent of nitrogen and from about 10 to 20 percent of propane, the latter three comprising the gaseous flame suppressor. It must be borne in mind that this example is given relative to the synthesis of acrylonitrile from propylene utilizing oxygen-enriched air containing approximately 60 percent by volume of oxygen as the oxygen containing feed to the ammoxidation reactor which is operating at 60 percent conversion of the propylene. More preferably, the volume percent of propylene, nitrogen and carbon monoxide in the quench tower effluent is from about 35 to 70 percent by volume. In the process illustrated in FIG. 3, the preferred selective separator is a PSA unit operating under pressure provided by a compressor. The compressor increases the pressure of the quench tower gaseous phase to the preferred operating pressure of a PSA unit, typically in the range of from about 3 to 50 psig, preferably from about 20 to 40 psig. The range of preferred operating pressure may vary to an extent depending on the adsorbent utilized.

The adsorbent in the PSA unit may be any art-recognized material which adsorbs propylene to a substantially greater degree than propane or carbon dioxide. Silica gel is a preferred adsorbent material.

By proper selection of the adsorbent in the PSA unit, the operation thereof can readily be controlled utilizing art-recognized manipulations so that the recycle stream formed therein contains a substantial portion of the propylene and lesser percentages of propane and carbon dioxide. The pressure of the recycle stream may be raised, e.g. via a compressor, such that a compressor may not be required in the inlet to the selective separator. The nitrogen, oxygen and the remainder of the carbon oxides and propane are withdrawn from the system, preferably combusted, and vented. It is contemplated herein to recover oxygen from the vent stream and recycle it to the reactor feed to enhance the operation of the system.

Utilizing a system, as shown in FIG. 3, for the production of acrylonitrile utilizing oxygen-enriched air containing approximately 60 percent by volume of oxygen as a reactor feed and a mixture of nitrogen, carbon dioxide and propane as the gaseous flame suppressor, with nitrogen comprising a major portion thereof, the flow rates in mole percent at critical points in the system were determined based on 100 moles of acrylonitrile produced and are presented in Tables I and II. The feed oxidant in Table I is obtained by mixing equal parts of air and pure oxygen, while the feed oxidant in Table II is air. The data expressed in Tables I and II represent operation of the system under conditions such that 60 percent and 90 percent, respectively, of the propylene feed to the ammoxidation reactor is converted to products. In Tables I and II, Point A is the feed into the ammoxidation reactor, Point B is effluent therefrom, Point C is the effluent from the quench tower, Point D is the recycle stream from the PSA separator, and Point E is the vent stream from the PSA separator.

TABLE I

| Component | A | B | C | D | E |
|---|---|---|---|---|---|
| 60 Percent Conversion - Equal parts pure oxygen and air | | | | | |
| Propylene | 15.3 | 5.8 | 9.2 | 30.4 | 0.3 |
| Propane | 8.2 | 7.8 | 12.4 | 40.8 | 0.5 |
| Oxygen | 21.1 | 4.0 | 6.4 | 0.4 | 8.9 |
| CO | — | 0.7 | 1.1 | 0.1 | 1.5 |
| CO$_2$ | 4.8 | 6.5 | 10.3 | 24.2 | 4.4 |
| Acrylonitrile | — | 7.2 | — | — | — |
| Acrolein | — | 0.1 | — | — | — |
| Acetonitrile | — | 0.1 | — | — | — |
| HCN | — | 1.2 | — | — | — |
| Water | — | 27.3 | — | — | — |
| Ammonia | 10.3 | 1.0 | — | — | — |
| Nitrogen | 40.3 | 38.2 | 60.6 | 4.1 | 84.4 |
| 90 Percent Conversion - Equal parts pure oxygen and air | | | | | |
| Propylene | 16.0 | 1.4 | 3.2 | 9.9 | 0.1 |
| Propane | 7.5 | 6.4 | 15.1 | 42.8 | 2.2 |
| Oxygen | 32.7 | 4.0 | 11.7 | — | 17.2 |
| CO | — | 1.1 | 2.6 | — | 3.8 |
| CO$_2$ | 7.4 | 10.4 | 24.4 | 47.1 | 13.9 |
| Acrylonitrile | — | 9.8 | — | — | — |
| Acrolein | — | 0.1 | — | — | — |
| Acetonitrile | — | 0.1 | — | — | — |
| HCN | — | 2.0 | — | — | — |
| Water | — | 45.2 | — | — | — |
| Ammonia | 15.0 | 1.0 | — | — | — |
| Nitrogen | 21.4 | 18.4 | 43.0 | 0.1 | 62.8 |

TABLE II

| Component | A | B | C | D | E |
|---|---|---|---|---|---|
| 60 Percent Conversion - Air | | | | | |
| Propylene | 10.3 | 4.0 | 5.4 | 30.8 | 0.2 |
| Propane | 2.6 | 2.5 | 3.4 | 19.1 | 0.2 |
| Oxygen | 15.6 | 4.0 | 5.4 | 1.6 | 6.2 |
| CO | — | 0.5 | 0.6 | 0.2 | 0.7 |
| CO$_2$ | 3.3 | 4.5 | 6.1 | 25.0 | 2.2 |
| Acrylonitrile | — | 5.0 | — | — | — |
| Acrolein | — | — | — | — | — |
| Acetonitrile | — | 0.1 | — | — | — |
| HCN | — | 1.0 | — | — | — |
| Water | — | 18.8 | — | — | — |
| Ammonia | 7.3 | 1.0 | — | — | — |
| Nitrogen | 60.9 | 58.6 | 79.1 | 23.4 | 90.5 |

TABLE II-continued

| Component | A | B | C | D | E |
|---|---|---|---|---|---|
| 90 Percent Conversion - Air | | | | | |
| Propylene | 7.0 | 0.7 | 0.9 | 9.8 | — |
| Propane | 3.3 | 3.1 | 4.2 | 42.5 | 0.5 |
| Oxygen | 16.6 | 4.0 | 6.9 | 0.1 | 7.6 |
| CO | — | 0.5 | 0.7 | — | 0.8 |
| CO$_2$ | 3.3 | 5.0 | 6.9 | 46.7 | 2.9 |
| Acrylonitrile | — | 4.7 | — | — | — |
| Acrolein | — | — | — | — | — |
| Acetonitrile | — | 0.1 | — | — | — |
| HCN | — | 1.0 | — | — | — |
| Water | — | 21.6 | — | — | — |
| Ammonia | 7.2 | 1.0 | — | — | — |
| Nitrogen | 62.6 | 58.4 | 80.4 | 0.9 | 88.2 |

The data in Tables I and II represent a typical commercial propylene source which comprised about 95 percent propylene with the remainder being propane.

Table III shows an example for the production of acrylonitrile from propane using equal parts of oxygen and air oxidant feed. The Points in Table III are the same as the Table I Points.

TABLE III

| Component | A | B | C | D | E |
|---|---|---|---|---|---|
| 67 Percent Conversion - Equal parts pure oxygen and air | | | | | |
| Propylene | 0.3 | 0.1 | 0.1 | 0.2 | — |
| Propane | 13.9 | 4.1 | 6.6 | 11.9 | 0.6 |
| Oxygen | 28.3 | 2.3 | 3.7 | 1.7 | 6.0 |
| CO | 0.4 | 1.3 | 2.1 | 1.0 | 3.4 |
| CO$_2$ | 24.5 | 29.3 | 47.6 | 66.9 | 26.2 |
| Acrylonitrile | — | 5.0 | — | — | — |
| Acrolein | — | 0.1 | — | — | — |
| Acetonitrile | — | 0.1 | — | — | — |
| HCN | — | 1.0 | — | — | — |
| Water | 1.0 | 34.9 | 5.7 | 2.7 | 8.9 |
| Ammonia | 7.9 | 1.0 | — | — | — |
| Nitrogen | 23.8 | 21.0 | 34.2 | 15.6 | 54.9 |

Figure 4:
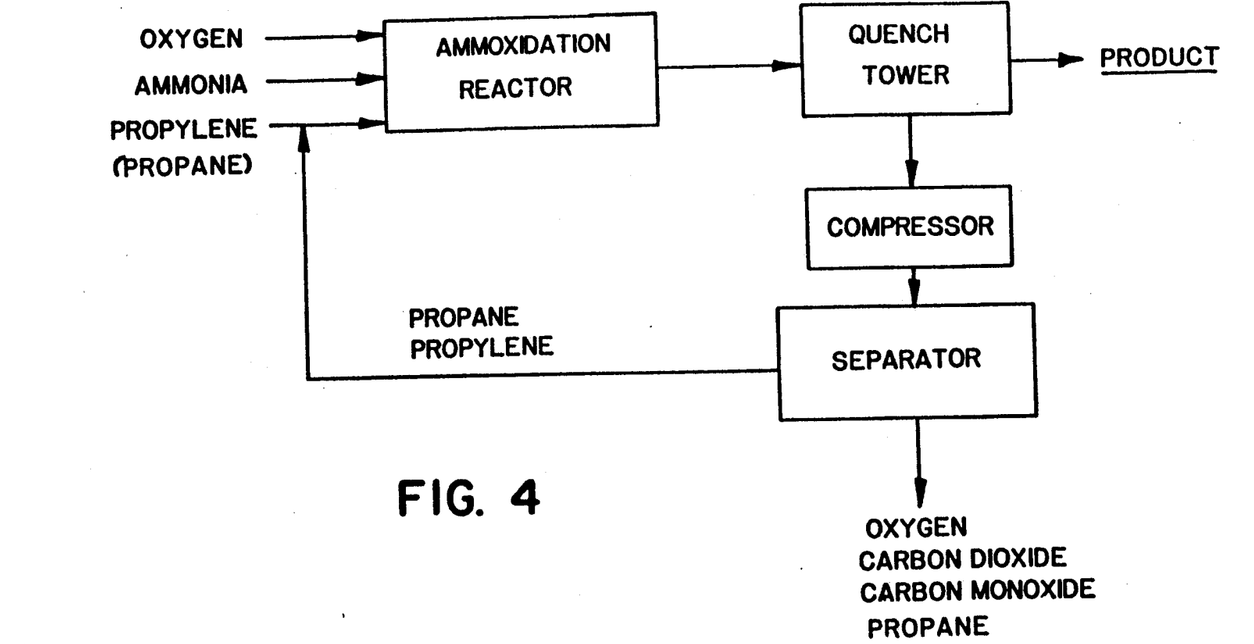
FIG. 4 illustrates in a block diagram an embodiment of a process of producing acrylonitrile in accordance with this invention wherein the gaseous flame suppressor contains a major portion of propane.

In FIG. 4, there is illustrated a system utilizing a pure oxygen feed to the reactor wherein the gaseous flame suppressor is comprises propane and carbon dioxide. On a volume-to-volume basis, propane is the most effective component of the subject gaseous flame suppressor mixtures. In the system shown in FIG. 4, the gas phase effluent from the quench tower is introduced into a separator, preferably a PSA unit, to separate the propylene and at least a portion of the propane for recycle to the combined reactor feed. As in the system shown in FIG. 3, the volume percent of propane in the reactor feed is determined so as to produce a concentration in the gaseous feed from the quench tower to the compressor which, in combination with the carbon dioxide present, will reduce flammability potential.

The gas phase effluent from the quench tower preferably contains, on a volume basis, from about 10 to 40 percent of propylene, from about 5 to 25 percent of oxygen, from about 10 to 45 percent of carbon dioxide, from about 2 to 5 percent of carbon monoxide and from about 5 to 50, preferably about 40 percent, of propane. More preferably, the combined volume percent of propylene, propane and carbon monoxide in the quench tower effluent is from about 35 to 70 percent by volume.

The amount of propane in the recycle stream can be the predetermined minimum amount previously given, but typically will be lower to compensate for the amount of propane present in the propylene supply as an impurity. The selective separation capacity of the PSA unit provides not only recycle of a substantial portion of the unreacted propylene to the reactor, but also for a relatively constant level of propane in the system.

Utilizing a system as shown in FIG. 4 for the production of acrylonitrile utilizing a gaseous flame suppressor mixture with propane as major component, the flow rates in mole percent at critical points in the system were determined and are presented in Table IV. The compositions are expressed in mole percent and based on 100 moles of acrylonitrile produced. The data expressed in Table IV represents operation of the system under conditions such that 60 percent and 90 percent, respectively, of the propylene feed to the ammoxidation reactor is converted to products. In Table IV, the various Points are the same as in Table I.

TABLE IV

| Component | A | B | C | D | E |
|---|---|---|---|---|---|
| 60 Percent Conversion | | | | | |
| Propylene | 27.8 | 9.3 | 28.0 | 39.4 | 2.3 |
| Propane | 8.8 | 7.4 | 22.3 | 28.8 | 7.4 |
| Oxygen | 36.7 | 5.0 | 15.0 | — | 49.1 |
| CO | — | 1.0 | 3.2 | — | 10.3 |
| $CO_2$ | 8.8 | 10.5 | 31.5 | 31.8 | 31.0 |
| Acrylonitrile | — | 11.6 | — | — | — |
| Acrolein | — | 0.1 | — | — | — |
| Acetonitrile | — | 0.2 | — | — | — |
| HCN | — | 2.3 | — | — | — |
| Water | — | 51.5 | — | — | — |
| Ammonia | 18.0 | 1.0 | — | — | — |
| 90 Percent Conversion | | | | | |
| Propylene | 20.6 | 1.7 | 5.9 | 9.9 | 0.3 |
| Propane | 9.7 | 8.0 | 27.6 | 43.0 | 6.6 |
| Oxygen | 41.0 | 4.0 | 17.2 | — | 40.7 |
| CO | — | 1.4 | 4.7 | — | 11.2 |
| $CO_2$ | 9.6 | 12.9 | 44.6 | 47.1 | 41.1 |
| Acrylonitrile | — | 12.1 | — | — | — |
| Acrolein | — | 0.1 | — | — | — |
| Acetonitrile | — | 0.2 | — | — | — |
| HCN | — | 2.5 | — | — | — |
| Water | — | 56.1 | — | — | — |
| Ammonia | 19.1 | 1.0 | — | — | — |

The data presented in Table IV represents a typical commercial propylene source which comprised about 95 percent propylene with the remainder being propane. The run was repeated utilizing high purity propylene which is about 98 percent pure. The results are reported in Table V.

TABLE V

| Component | A | B | C | D | E |
|---|---|---|---|---|---|
| 60 Percent Conversion | | | | | |
| Propylene | 29.5 | 9.8 | 32.6 | 47.6 | 2.5 |
| Propane | 3.8 | 3.1 | 10.4 | 14.0 | 3.2 |
| Oxygen | 38.5 | 5.0 | 16.6 | — | 50.1 |
| CO | — | 1.1 | 3.7 | — | 11.1 |
| $CO_2$ | 9.3 | 11.0 | 36.7 | 38.4 | 33.2 |
| Acrylonitrile | — | 12.2 | — | — | — |
| Acrolein | — | 0.1 | — | — | — |
| Acetonitrile | — | 0.2 | — | — | — |
| HCN | — | 2.4 | — | — | — |
| Water | — | 54.0 | — | — | — |
| Ammonia | 25.0 | 1.0 | — | — | — |
| 90 Percent Conversion | | | | | |
| Propylene | 22.0 | 1.8 | 7.1 | 13.4 | 0.4 |
| Propane | 4.0 | 3.3 | 13.0 | 23.0 | 2.7 |
| Oxygen | 43.5 | 4.0 | 19.9 | — | 41.1 |
| CO | — | 1.5 | 5.8 | — | 11.4 |
| $CO_2$ | 10.2 | 13.7 | 54.3 | 65.3 | 41.8 |
| Acrylonitrile | — | 12.7 | — | — | — |
| Acrolein | — | 0.1 | — | — | — |
| Acetonitrile | — | 0.2 | — | — | — |
| HCN | — | 2.7 | — | — | — |
| Water | — | 59.1 | — | — | — |
| Ammonia | 20.3 | 1.0 | — | — | — |

Figure 5:
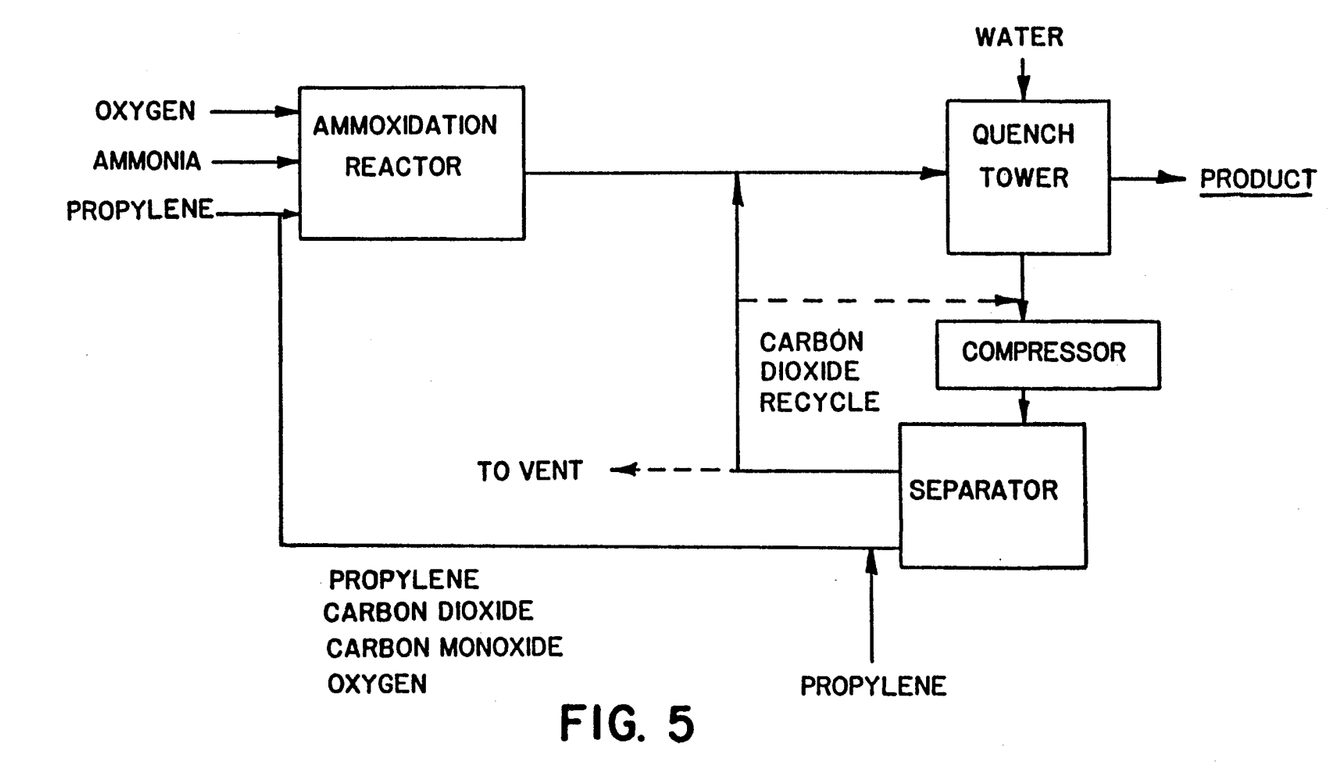
FIG. 5 illustrates in a block diagram an embodiment of a process of producing acrylonitrile in accordance with this invention wherein the gaseous flame suppressor contains a major portion of carbon dioxide.

In the embodiment of the present invention illustrated in FIG. 5, a pure oxygen feed to the ammoxidation reactor is utilized with a gaseous flame suppressor mixture containing carbon dioxide as the major component. In this instance, the percent of carbon dioxide in the feed to the selective separator is from about 25 to 70, preferably from about 35 to 65, percent by volume. The selective separator may be a PSA unit or a conventional liquid separator operating on the well-known Benfield process wherein carbon dioxide is removed from the effluent by dissolution in an absorbent solution, such as potassium carbonate. In either instance, however, although the separator may be run at ambient pressure, it is preferred that the feed to the separator be introduced under pressure utilizing, e.g. a compressor, as shown in FIG. 5. When a liquid separator is utilized, the resultant solution is regenerated to release carbon dioxide. Wherein the separator is a PSA unit, the adsorbent is suitably a zeolite molecular sieve such as 4A molecular sieve or a silic gel, preferably the latter.

Since carbon dioxide is produced in the ammoxidation reactor as an undesirable by-product, it is preferred to have only a small quantity thereof recycled in the reactor feed. In addition, it is advantageous to minimize the carbon dioxide content in the reactor to prevent an undesirable pressure build-up which would decrease the efficiency of the process. Typically, the feed to the ammoxidation reactor comprises propylene, oxygen, ammonia and about 5 percent by volume or less of carbon dioxide.

In the embodiment shown in FIG. 5, carbon dioxide separated in the separator is at least partially recycled upstream of the compressor to assure that the concentration entering the compressor is from about 25 to 70 percent by volume. Since it is not necessary to have a high initial concentration of carbon dioxide in the reactor, the recycle thereof is within the system to achieve the desired concentration thereof in the gaseous flame suppressor. The recycle may reenter the system either upstream or downstream of the quench tower or at both locations as shown in FIG. 5. In the event that the concentration of carbon dioxide in the stream entering the compressor becomes too great, a portion of the recycle stream is vented from the system as shown in FIG. 5. The operating pressure of the selective separator is typically from about 10 to 50, preferably from about 20 to 40, psig. The recycle of carbon dioxide as shown in FIG. 5 is carried out even in those instances where the selective separator is operated at close to ambient pressure and there is no compressor in the system since it provides better control over the amount of carbon dioxide in the system.

The gas mixture exiting the selective separator comprises carbon dioxide, carbon monoxide, oxygen and unreacted propylene. A Benfield process selective separator will generally reduce the carbon dioxide content of the effluent gas mixture to about 5 percent by volume. A PSA unit selective separator will generally reduce the carbon dioxide content of the effluent to about 10 percent by volume. Unreacted reactant hydrocarbon is also present in the system to a degree varying with the reactor conversion as disclosed above and is substantially all recycled from the selective separator. Fresh reactant hydrocarbon is added to this mixture to increase the pressure thereof, if necessary, and it is recycled to the ammoxidation reactor where it is combined with incoming oxygen, ammonia and additional reactant hydrocarbon, e.g. propylene, to produce a final carbon dioxide concentration of about 1 percent or less by volume.

Table VI gives an indication of the operating parameters of a system for the synthesis of acrylonitrile as shown in FIG. 5 wherein carbon dioxide is a major component of the gaseous flame suppressor and the selective separator is a conventional liquid separator. As in the previous Tables, the data in Table VI are expressed in mole percent based on 100 of acrylonitrile produced. The data in Table VI are also for 60 and 90 percent propylene per pass conversion and are for the following points in the process: A is feed into the ammoxidation reactor; B is effluent therefrom; C is effluent from the quench tower prior to the addition of recycled carbon dioxide thereto; D is the feed to the compressor; E is the recycle stream from the separator to the reactor; and F is the carbon dioxide recycle from the selective separator.

TABLE VI

| Component | A | B | C | D | E | F |
|---|---|---|---|---|---|---|
| 60 Percent Conversion | | | | | | |
| Propylene | 33.3 | 11.9 | 52.4 | 33.4 | 65.4 | 0.8 |
| Propane | 1.5 | 1.3 | 5.7 | 3.6 | 1.9 | 0.1 |
| Oxygen | 42.8 | 5.0 | 21.9 | 14.0 | 25.9 | 0.3 |
| CO | 1.1 | 2.0 | 4.7 | 3.0 | 5.6 | 0.1 |
| $CO_2$ | 0.2 | 3.7 | 15.3 | 45.9 | 1.2 | 98.7 |
| Acrylonitrile | — | 15.4 | — | — | — | — |
| Acrolein | — | 0.1 | — | — | — | — |
| Acetonitrile | — | 0.2 | — | — | — | — |
| HCN | — | 2.4 | — | — | — | — |
| Water | — | 57.0 | — | — | — | — |
| Ammonia | 21.1 | 1.0 | — | — | — | — |
| 90 Percent Conversion | | | | | | |
| Propylene | 24.2 | 2.1 | 12.6 | 6.0 | 23.6 | 0.1 |
| Propane | 1.5 | 1.4 | 8.0 | 3.8 | 4.0 | 0.1 |
| Oxygen | 50.6 | 5.0 | 29.4 | 14.0 | 52.3 | 0.2 |
| CO | 1.6 | 3.0 | 9.2 | 4.4 | 16.3 | 0.1 |
| $CO_2$ | 0.3 | 7.2 | 40.8 | 71.8 | 3.8 | 99.5 |
| Acrylonitrile | — | 15.2 | — | — | — | — |
| Acrolein | — | 0.1 | — | — | — | — |
| Acetonitrile | — | 0.2 | — | — | — | — |
| HCN | — | 2.9 | — | — | — | — |
| Water | — | 61.9 | — | — | — | — |
| Ammonia | 21.8 | 1.0 | — | — | — | — |

In Table VII, the system is as shown in FIG. 5, but utilizing a PSA unit as a separator. In Table VII, points A through D are as in Table VI, Point E is the recycle gaseous stream from the PSA unit, and point F is the $CO_2$ recycle stream from the PSA unit.

TABLE VII

| Component | A | B | C | D | E | F |
|---|---|---|---|---|---|---|
| 60 Percent Conversion | | | | | | |
| Propylene | 32.9 | 11.8 | 52.2 | 33.1 | 63.5 | 7.4 |
| Propane | 1.4 | 1.3 | 5.7 | 3.6 | 1.8 | 0.8 |
| Oxygen | 43.0 | 5.0 | 22.1 | 14.0 | 25.4 | 3.1 |
| CO | 1.0 | 2.0 | 4.7 | 3.0 | 5.4 | 0.7 |
| $CO_2$ | 0.8 | 4.1 | 15.3 | 46.3 | 3.9 | 88.0 |
| Acrylonitrile | — | 15.3 | — | — | — | — |
| Acrolein | — | 0.1 | — | — | — | — |
| Acetonitrile | — | 0.1 | — | — | — | — |
| HCN | — | 2.4 | — | — | — | — |
| Water | — | 56.9 | — | — | — | — |
| Ammonia | 20.9 | 1.0 | — | — | — | — |
| 90 Percent Conversion | | | | | | |
| Propylene | 23.6 | 2.1 | 12.5 | 5.9 | 21.0 | 0.9 |
| Propane | 1.5 | 1.3 | 8.0 | 3.7 | 3.6 | 0.6 |
| Oxygen | 50.9 | 5.0 | 29.8 | 14.0 | 48.4 | 2.2 |
| CO | 1.5 | 2.9 | 9.1 | 4.3 | 14.9 | 0.7 |
| $CO_2$ | 1.2 | 7.9 | 40.6 | 72.1 | 11.5 | 95.6 |
| Acrylonitrile | — | 15.0 | — | — | — | — |
| Acrolein | — | 0.1 | — | — | — | — |
| Acetonitrile | — | 0.2 | — | — | — | — |
| HCN | — | 2.8 | — | — | — | — |
| Water | — | 61.7 | — | — | — | — |
| Ammonia | 21.3 | 1.0 | — | — | — | — |

It will be appreciated that, when carbon dioxide or a substantially unreactive hydrocarbon is the major component of the gaseous flame suppressor in the process of the present invention, it will be necessary initially to add a sufficient amount thereof to the feed to the ammoxidation or oxidation reactor to establish the desired concentration thereof, i.e. to prime the system. This is, however, not necessary utilizing oxygen-enriched air as the reactor feed wherein nitrogen is the major component of the gaseous flame suppressor. It will likewise be appreciated that it is within the scope of the present invention to utilize conventional equipment to monitor and automatically regulate the flow of gases within the system so that it can be fully automated to run continuously in an efficient manner.

The process of this invention is advantageous in its simplicity, ease of operation, low capital and operating costs as well as providing a substantially reduced flammability potential. In the process illustrated in FIG. 3, it is possible to utilize a less expensive grade of propylene which contains appreciable quantities of propane as an impurity. Likewise, the use of air or oxygen-enriched air as a starting material wherein nitrogen is the major component of the gaseous flame suppressor, provides further economic savings. The subject process can be run at a relatively low conversion of the feed hydrocarbon to the desired product to achieve substantially improved selectivity for the subject process. It will be appreciated that a system that runs at comparatively reduced conversion per pass and achieves enhanced selectivity to a desired product utilizing a less expensive grade of feed materials is highly advantageous.

We claim:

1. A cyclic process for the production of alpha, beta olefinically unsaturated nitriles comprising:
   (a) reacting a reactant from the group consisting of an alkane or alkene, an oxygen-containing gas, and ammonia in the vapor phase in the presence of an ammoxidation catalyst in a reactor vessel under conditions which produce an effluent containing the nitrile at low feed conversion and high product selectivity;
   (b) quenching the effluent with a liquid to form a quenched liquid phase containing said nitrile and a gaseous phase containing gaseous products including unreacted reactant;
   (c) recovering said nitrile from the liquid phase;
   (d) introducing the gaseous phase as a pressurized feed into a selective separator to thereby remove a substantial portion of the unreacted reactant; and
   (e) recycling said unreacted reactant under pressure to said reactor vessel, wherein the process is conducted in the presence of a gaseous flame suppressor, the process being controlled so that flame suppression will be maximized at the point in the process where the pressure is increased, the amount of flame suppressor being such that the gaseous phase formed in step (b) contains from about 30 to about 95 percent by volume thereof.

2. A process in accordance with claim 1, wherein the oxygen-containing gas is selected from the group consisting of pure oxygen, air, and a gas enriched in oxygen relative to air.

3. A process in accordance with claim 2, wherein the oxygen-containing gas is air or a gas enriched in oxygen relative to air, and said gaseous flame suppressor comprises a substantially unreactive hydrocarbon containing 1 to 5 carbon atoms, carbon dioxide, and nitrogen.

4. A process in accordance with claim 3, wherein said substantially unreactive hydrocarbon is a saturated hydrocarbon.

5. A process in accordance with claim 2, wherein the oxygen-containing gas is pure oxygen and said gaseous flame suppressor comprises carbon dioxide and a substantially unreactive hydrocarbon containing 1 to 5 carbon atoms.

6. A process in accordance with claim 1, wherein said selective separator is a pressure swing adsorption unit.

7. A process in accordance with claim 6, wherein said pressure swing adsorption unit contains an adsorbent consisting of a silica gel or a zeolite molecular sieve.

8. A process in accordance with claim 5, wherein carbon dioxide is a major component of said gaseous flame suppressor and said selective separator is a liquid separator wherein carbon dioxide is removed from the gaseous phase by dissolution into an absorbent solution.

9. A process in accordance with claim 8, wherein the absorbent solution is an aqueous potassium carbonate solution.

10. A process in accordance with claim 9, wherein at least a portion of the carbon dioxide obtained in said separator is recycled to the effluent formed in step (a), the gas phase formed in step (b), or both of said effluent and said gas phase.

11. A process in accordance with claim 1, wherein the nitrile is acrylonitrile, the reactant alkene is propylene, the gaseous flame suppressor comprises carbon dioxide, propane, and nitrogen, and said oxygen-containing gas is air or a gas enriched in oxygen relative to air.

12. A process in accordance with claim 5, wherein the nitrile is acrylonitrile, the reactant alkene is propylene the gaseous flame suppressor is carbon dioxide and propane, the gas phase formed in step (b) comprises unreacted propylene, oxygen, carbon dioxide, carbon monoxide and from about 5 to 50 volume percent of propane, and the selective separator is a pressure swing adsorption unit.

13. A process in accordance with claim 1, wherein the nitrile is acrylonitrile, the reactant alkane is propane, the gaseous flame suppressor comprises carbon dioxide, methane, ethane, and nitrogen, and said oxygen-containing gas is air or a gas enriched in oxygen relative to air.

14. A process in accordance with claim 5, wherein the nitrile is acrylonitrile, the reactant alkane is propane, and the gaseous flame suppressor is carbon dioxide, methane, and ethane, the gas phase formed in step (b) comprises unreacted propane, oxygen, carbon dioxide, carbon monoxide and from about 5 to 50 volume percent of methane and ethane, and the selective separator is a pressure swing adsorption unit.

15. A process in accordance with claim 1, wherein the nitrile is methacrylonitrile, the reactant alkene is isobutylene, the gaseous flame suppressor comprises carbon dioxide, methane, ethane, isobutane, and nitrogen, and said oxygen-containing gas is air or a gas enriched in oxygen relative to air.

16. A process in accordance with claim 5, wherein the nitrile is methacrylonitrile, the reactant alkene is isobutylene, the gaseous flame suppressor is carbon dioxide, methane, ethane, and isobutane, the gas phase formed in step (b) comprises unreacted isobutylene, oxygen, carbon dioxide, carbon monoxide and from about 5 to 50 volume percent of methane, ethane and isobutane, and the selective separator is a pressure swing adsorption unit.

17. A process in accordance with claim 1, wherein the nitrile is methacrylonitrile, the reactant alkane is isobutane, the gaseous flame suppressor comprises carbon dioxide, methane, ethane, and nitrogen, and said oxygen-containing gas is air or a gas enriched in oxygen relative to air.

18. A process in accordance with claim 5, wherein the nitrile is methacrylonitrile, the reactant alkane is isobutane, the gaseous flame suppressor is carbon dioxide, methane, and ethane, the gas phase formed in step (b) comprises unreacted isobutane, oxygen, carbon dioxide, carbon monoxide and from about 5 to 50 volume percent of methane and ethane, and selective separator is a pressure swing absorption unit.

19. A cyclic process for the production of benzene nitriles comprising:
(a) reacting a reactant xylene, and oxygen-containing gas, and ammonia in the vapor phase in the presence of an ammoxidation catalyst in a reactor vessel under conditions which produce an effluent containing the nitrile at low feed conversion and high product selectivity;
(b) quenching the effluent with a liquid to form a quenched liquid phase containing said nitrile and a gaseous phase containing gaseous products including unreacted reactant;
(c) recovering said nitrile from the liquid phase;
(d) introducing the gaseous phase as a pressurized feed into a selective separator to thereby remove a substantial portion of the unreacted reactant; and
(e) recycling said unreacted reactant under pressure to said reactor vessel, wherein the process is conducted in the presence of a gaseous flame suppressor, the process being controlled so that flame suppression will be maximized at the point in the process where the pressure is increased, the amount of flame suppressor being such that the gaseous phase formed in step (b) contains from about 30 to about 95 percent volume thereof.

20. A process in accordance with claim 19, wherein the nitrile is phthalonitrile, the reactant xylene is orthoxylene, the gaseous flame suppressor comprises carbon dioxide, methane, and nitrogen, and said oxygen containing gas is air or a gas enriched in oxygen relative to air.

21. A process in accordance with claim 19, wherein the nitrile is phthalonitrile, the reactant xylene is orthoxylene, the gaseous flame suppressor is carbon dioxide and methane, the gas phase formed in step (b) comprises unreacted orthoxylene, oxygen, carbon dioxide, carbon monoxide and from about 5 to 50 volume percent of methane, and the selective separator is a pressure swing adsorption unit.

* * * * *